US00PP32696P2

(12) United States Plant Patent
Danziger

(10) Patent No.: US PP32,696 P2
(45) Date of Patent: Dec. 22, 2020

(54) ***SANVITALIA* PLANT NAMED 'DSANTALG'**

(50) Latin Name: *Sanvitalia speciosa*
Varietal Denomination: DSANTALG

(71) Applicant: Gavriel Danziger, Moshav Mishmar Hashiva (IL)

(72) Inventor: Gavriel Danziger, Moshav Mishmar Hashiva (IL)

(73) Assignee: DANZIGER "DAN" FLOWER FARM, Beit Dagan (IL)

( * ) Notice: Subject to any disclaimer, the term of this patent is extended or adjusted under 35 U.S.C. 154(b) by 0 days.

(21) Appl. No.: 16/873,353

(22) Filed: Mar. 26, 2020

(51) Int. Cl.
*A01H 5/02* (2018.01)
*A01H 6/14* (2018.01)

(52) U.S. Cl.
USPC ..... Plt./476

(58) Field of Classification Search
USPC ..... Plt./263.1, 476
See application file for complete search history.

*Primary Examiner* — Susan McCormick Ewoldt
(74) *Attorney, Agent, or Firm* — C. A. Whealy

(57) ABSTRACT

A new and distinct cultivar of *Sanvitalia* plant named 'DSANTALG', characterized by its mounding to semi-trailing plant habit; moderately vigorous growth habit; early and freely flowering habit; inflorescences with golden yellow-colored ray florets and yellow green to bright yellow-colored disc florets; and good garden performance.

2 Drawing Sheets

Figure 1:
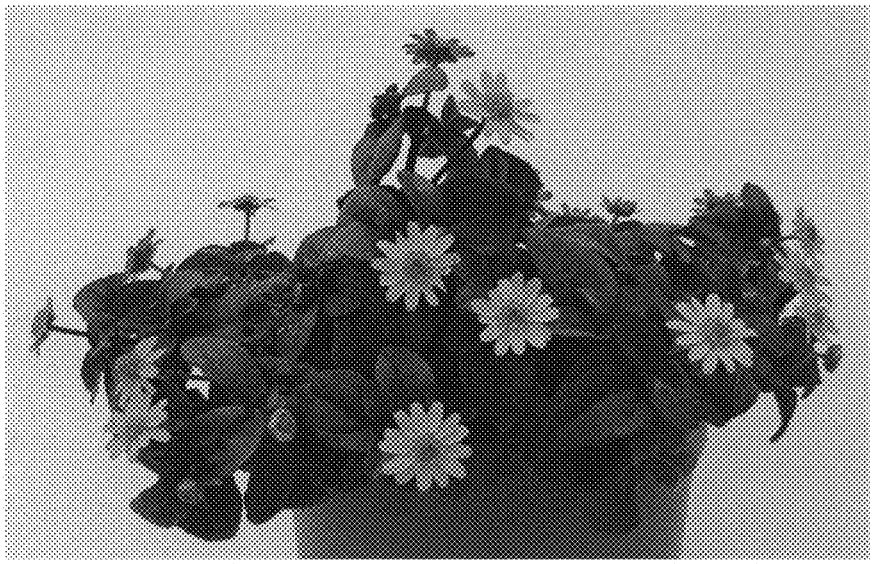

Botanical designation: *Sanvitalia speciosa.*
Cultivar denomination: 'DSANTALG'.

BACKGROUND OF THE INVENTION

The present invention relates to a new and distinct cultivar of *Sanvitalia* plant, botanically known as *Sanvitalia speciosa*, and hereinafter referred to by the name 'DSANTALG'.

The new *Sanvitalia* plant is a product of a planned breeding program conducted by the Inventor in Nir-Zvi and Mishmar Hashiva, Israel. The objective of the breeding program is to create new compact mounding *Sanvitalia* plants that flower early and have numerous attractive inflorescences.

The new *Sanvitalia* plant originated from an open-pollination in Nir-Zvi, Israel of a proprietary selection of *Sanvitalia speciosa* identified as code number SN-14-697, not patented, as the female, or seed, parent with an unknown selection of *Sanvitalia speciosa* as the male, or pollen, parent. The new *Sanvitalia* plant was discovered and selected by the Inventor as a single flowering plant from within the progeny of the stated open-pollination in a controlled greenhouse environment in Mishmar Hashiva, Israel on Jan. 15, 2017.

Asexual reproduction of the new *Sanvitalia* plant by vegetative terminal cuttings in a controlled environment in Mishmar Hashiva, Israel since Jan. 15, 2017 has shown that the unique features of this new *Sanvitalia* plant are stable and reproduced true to type in successive generations.

SUMMARY OF THE INVENTION

Plants of the new *Sanvitalia* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'DSANTALG'. These characteristics in combination distinguish 'DSANTALG' as a new and distinct *Sanvitalia* plant:

1. Mounding to semi-trailing plant habit.
2. Moderately vigorous growth habit.
3. Early and freely flowering habit.
4. Inflorescences with golden yellow-colored ray florets and yellow green to bright yellow-colored disc florets.
5. Good garden performance.

Plants of the new *Sanvitalia* differ primarily from plants of the female parent selection in plant habit as plants of the new *Sanvitalia* are more mounding than plants of the female parent selection. In addition, leaves of plants of the new *Sanvitalia* are darker green in color than leaves of plants of the female parent selection.

Plants of the new *Sanvitalia* can be compared to plants of *Sanvitalia speciosa* 'Aztek Gold', not patented. In side-by-side comparisons plants of the new *Sanvitalia* differ primarily from plants of 'Aztek Gold' in the following characteristics:

1. Plants of the new *Sanvitalia* are more mounding and semi-trailing than plants of 'Aztek Gold'.
2. Plants of the new *Sanvitalia* are more freely branching than plants of 'Aztek Gold'.
3. Plants of the new *Sanvitalia* are more freely flowering than plants of 'Aztek Gold'.

Plants of the new *Sanvitalia* can also be compared to plants of *Sanvitalia speciosa* 'Talya Great Yellow', not patented. In side-by-side comparisons plants of the new *Sanvitalia* differ primarily from plants of 'Talya Great Yellow' in the following characteristics:

1. Plants of the new *Sanvitalia* are more semi-trailing than plants of 'Talya Great Yellow'.
2. Leaves of plants of the new *Sanvitalia* are broader and darker green in color than leaves of plants of 'Talya Great Yellow'.
3. Plants of the new *Sanvitalia* have smaller inflorescences than plants of 'Talya Great Yellow'.

4. Ray florets of plants of the new *Sanvitalia* are broader than ray florets of plants of 'Talya Great Yellow'.

BRIEF DESCRIPTION OF THE PHOTOGRAPHS

The accompanying photographs illustrate the overall appearance of the new *Sanvitalia* plant showing the colors as true as it is reasonably possible to obtain in colored reproductions of this type. Colors in the photographs may differ slightly from the color values cited in the detailed botanical description which accurately describe the colors of the new *Sanvitalia* plant.

The photograph on the first sheet (FIG. 1 of 2) is a side perspective view of a typical flowering plant of 'DSANTALG' grown in a container.

Figure 2:
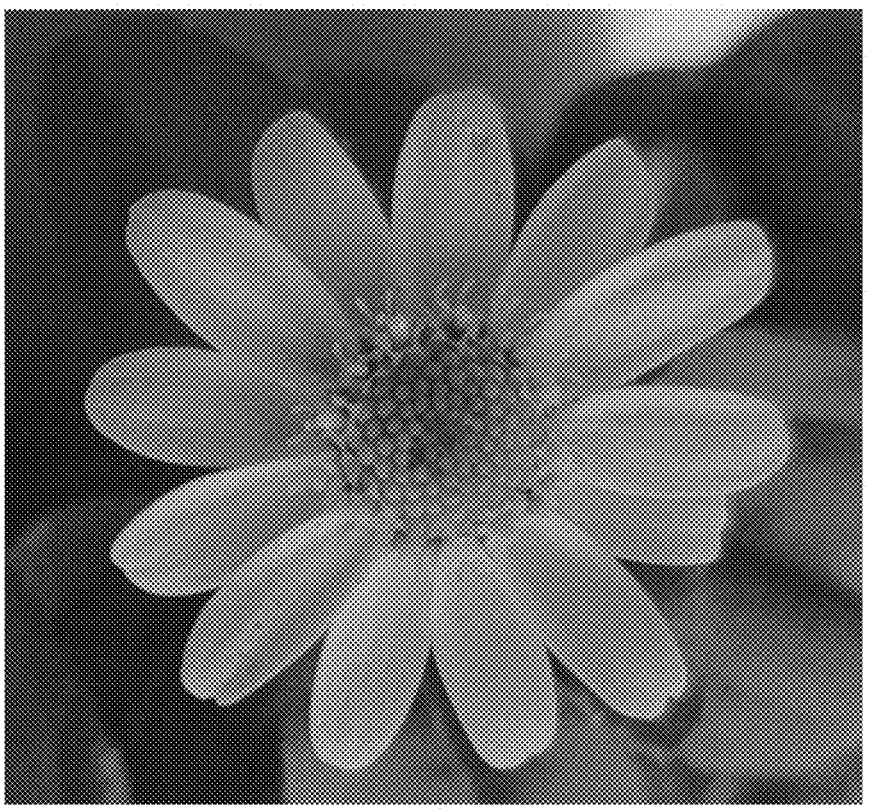

The photograph on the second sheet (FIG. 2 of 2) is a close-up view of a typical inflorescences of 'DSANTALG'.

DETAILED BOTANICAL DESCRIPTION

The aforementioned photographs and following observations and measurements describe plants grown during the autumn in 13-cm containers in a polyethylene-covered greenhouse and finished in an outdoor nursery in Nir-Zvi, Israel under conditions and practices which approximate those generally used in commercial *Sanvitalia* production. During the production of the plants, day temperatures ranged from 17° C. to 25° C., night temperatures ranged from 7° C. to 18° C. and light levels averaged 4,500 lux. Plants were pinched one time four days before planting and were eight weeks from planting when the photographs were taken and ten weeks from planting when the description was taken. In the following description, color references are made to The Royal Horticultural Society Colour Chart, 2007 Edition, except where general terms of ordinary dictionary significance are used Botanical classification: *Sanvitalia speciosa* 'DSANTALG'.

Parentage:

*Female parent*.—Proprietary selection of *Sanvitalia speciosa* identified as code number SN-14-697, not patented.

*Male parent*.—Unknown selection of *Sanvitalia speciosa*, not patented.

Propagation:

*Type*.—By vegetative terminal cuttings.

*Time to initiate roots, summer*.—About 12 to 14 days at ambient temperatures about 20° C.

*Time to initiate roots, winter*.—About 16 days at ambient temperatures about 16° C.

*Time to produce a rooted young plant, summer*.—About four to five weeks at ambient temperatures about 26° C.

*Time to produce a rooted young plant, winter*.—About six weeks at ambient temperatures about 18° C.

*Root description*.—Medium in thickness, fibrous; color, close to 155B.

*Rooting habit*.—Freely branching; moderately dense.

Plant description:

*Plant and growth habit*.—Mounding and semi-trailing plant habit; moderately vigorous growth habit and moderate growth rate.

*Branching habit*.—Freely branching habit with about five primary lateral branches per plant each with about nine secondary lateral branches.

*Plant height, soil level to tope of foliar plane*.—About 12 cm.

*Plant height, soil level to tope of floral plane*.—About 14 cm.

*Plant diameter or spread*.—About 20 cm.

*Lateral branches*.—Length: About 16 cm. Diameter: Proximally, about 4 mm to 5 mm and distally, about 2 mm to 3 mm. Internode length: About 3 cm. Strength: Strong, flexible. Aspect: Initially, about 35° from vertical and with development, closer to 60° from vertical. Texture and luster: Puberulent; semi-glossy. Color: Close to 145A; proximally, close to 59B.

Leaf description:

*Arrangement*.—Opposite, simple; sessile.

*Length*.—About 3 cm to 4 cm.

*Width*.—About 2 cm to 2.7 cm.

*Shape*.—Elliptical to oval.

*Apex*.—Rounded.

*Base*.—Obtuse.

*Margin*.—Entire.

*Texture, upper surface*.—Pubescent, rough.

*Texture, lower surface*.—Smooth, glabrous.

*Venation pattern*.—Pinnate.

*Color*.—Developing leaves, upper surface: Close to 137B. Developing leaves, lower surface: Close to 147C. Fully expanded leaves, upper surface: Close to 137A; venation, close to 137A. Fully expanded leaves, lower surface: Close to 147C; venation, close to 147C.

Inflorescence description:

*Form and aspect*.—Single (daisy) inflorescence form with ray and disc florets developing acropetally on a pyramidal receptacle; inflorescences positioned above and beyond the foliar plane on strong peduncles; inflorescences face mostly upright to outwardly.

*Flowering habit*.—Freely flowering habit; about 50 inflorescences developing per plant; about four open inflorescences per lateral branch.

*Fragrance*.—None detected.

*Natural flowering season*.—Plants flower continuously from the spring until the autumn in Israel; early flowering habit, plants begin flowering about 25 days after planting.

*Inflorescence longevity*.—Inflorescences last about four days on the plant; inflorescences persistent.

*Inflorescence buds*.—Height: About 2.3 mm. Diameter: About 5 mm. Shape: Oblate. Texture: Smooth, glabrous. Color: Close to 144A.

*Inflorescence size*.—Diameter: About 2.4 cm. Depth (height): About 5 mm to 6 mm. Disc diameter: About 7 mm. Receptacle diameter: About 1.5 mm. Receptacle height: About 1 mm. Receptacle color: Close to 144B to 144C.

*Ray florets*.—Number of ray florets per inflorescence: About 13 arranged in a single whorl. Length: About 7 mm. Width: About 3 mm. Shape: Elliptical. Apex: Emarginate or obtuse. Base: Cordate. Margin: Entire. Texture, upper and lower surfaces: Smooth, glabrous; satiny. Color: When opening and fully opened, upper surface: Close to 13A; venation, close to 13A; color does not change with development. When opening and fully opened, lower surface: Close to 12B; venation, close to 144C; color does not change with development.

*Disc florets*.—Number of disc florets per inflorescence: About 50, massed at the center of the inflorescence. Length: About 2.5 mm. Diameter: About 1 mm. Shape: Tubular, elongated; apex dentate. Texture: Smooth, glabrous. Color: Immature, inner surface: Close to 144A. Immature, outer surface: Close to 12D. Mature, inner surface: Close to 12B; color becoming closer to 12A with development. Mature, outer surface: Close to 12D; color does not change with development.

*Phyllaries*.—Quantity per inflorescence: About five in a single whorl. Length: About 7 mm. Width: About 5 mm. Shape: Elliptic. Apex: Acute. Base: Cuneate. Margin: Entire. Texture, upper and lower surfaces: Smooth, glabrous. Color, upper surface: Close to 144A. Color, lower surface: Close to 144C.

*Peduncles*.—Length, terminal peduncle: About 2.2 cm to 2.5 cm. Diameter, terminal peduncle: About 1 mm. Strength: Strong; flexible. Aspect: Upright to outwardly. Texture: Strigose. Color: Close to 59C.

*Reproductive organs*.—Androecium (present on disc florets only): Quantity per disc floret: Five. Filament length: About 0.5 mm. Filament color: Close to 1C. Anther size: About 1 mm by 0.2 mm. Anther shape: Oblong. Anther color: Close to 12A. Pollen amount: Scarce. Pollen color: Close to 3A. Gynoecium (present on ray and disc florets): Pistil length: About 2.4 mm. Style length: About 1.4 mm. Style color: Close to 12B. Stigma diameter: About 1 mm. Stigma shape: Bi-parted. Stigma color: Close to 12A. Ovary color: Close to 145D.

*Seeds*.—To date, seed development has not been observed on plants of the new *Sanvitalia*.

Pathogen & pest resistance: Plants of the new *Sanvitalia* have not been shown to be resistant to pathogens and pests common to *Sanvitalia* plants.

Garden performance: Plants of the new *Clematis* have exhibited good tolerance to rain and wind and have been observed to tolerate temperatures from about 6° C. to about 35° C.

It is claimed:

1. A new and distinct *Sanvitalia* plant named 'DSANTALG' as illustrated and described.

* * * * *